(12) United States Patent
Zadeh et al.

(10) Patent No.: US 6,658,294 B1
(45) Date of Patent: Dec. 2, 2003

(54) IMPLANTABLE CARDIAC DEVICE HAVING AN IMPEDANCE MONITORING CIRCUIT AND METHOD

(75) Inventors: Ali Enayat Zadeh, Sierra Madre, CA (US); Dro Darbidian, Tujunga, CA (US); George I. Isaac, Port Hueneme, CA (US)

(73) Assignee: Pacesetter, Inc., Sylmar, CA (US)

( * ) Notice: Subject to any disclaimer, the term of this patent is extended or adjusted under 35 U.S.C. 154(b) by 112 days.

(21) Appl. No.: 09/943,145

(22) Filed: Aug. 29, 2001

(51) Int. Cl.[7] .................................................. A61N 1/18
(52) U.S. Cl. ............................................................ 607/28
(58) Field of Search ................................ 607/4, 5, 7, 8, 607/27, 28; 328/63; 341/161; 600/547

(56) References Cited

U.S. PATENT DOCUMENTS

| | | | |
|---|---|---|---|
| 4,899,750 A | 2/1990 | Ekwall | 128/419 PG |
| 5,722,997 A | 3/1998 | Nedungadi et al. | 607/28 |
| 5,881,130 A * | 3/1999 | Zhang | 379/6 |
| 5,897,577 A | 4/1999 | Cinbis et al. | 607/28 |
| 5,910,156 A | 6/1999 | Cinbis et al. | 607/27 |
| 5,944,746 A | 8/1999 | Kroll | 607/27 |
| 6,287,263 B1 * | 9/2001 | Briskin | 600/526 |
| 6,502,046 B1 * | 12/2002 | Yoon et al. | 702/76 |
| 2001/0007056 A1 * | 7/2001 | Linder et al. | 607/5 |

* cited by examiner

*Primary Examiner*—Mark Bockelman

(57) ABSTRACT

A circuit within an implantable cardiac stimulation device monitors impedance of an electrode configuration including first and second electrodes in electrical contact with a heart. The circuit is within the implantable cardiac stimulation device which applies stimulation pulses having a current and a voltage magnitude across the electrode configuration. The circuit that monitors impedance of an electrode configuration provides an impedance digital output proportional to the ratio of a stimulation pulse voltage and current.

10 Claims, 3 Drawing Sheets

IMPLANTABLE CARDIAC DEVICE HAVING AN IMPEDANCE MONITORING CIRCUIT AND METHOD

FIELD OF THE INVENTION

The present invention generally relates to an implantable cardiac stimulation device. The present invention more particularly relates to an implantable cardiac stimulation device including a circuit for monitoring impedance of an electrode configuration and providing an impedance digital output proportional to the ratio of a stimulation pulse voltage and current.

BACKGROUND OF THE INVENTION

Implantable cardiac devices are well known in the art. They may take the form of implantable defibrillators or cardioverters which treat accelerated rhythms of the heart such as fibrillation or implantable pacemakers which maintain the heart rate above a prescribed limit, such as, for example, to treat a bradycardia. Implantable cardiac devices are also known which incorporate both a pacemaker and a defibrillator.

A pacemaker may be considered as a pacing system. The pacing system is comprised of two major components. One component is a pulse generator which generates the pacing stimulation pulses and includes the electronic circuitry and the power cell or battery. The other component is the lead, or leads, which electrically couple the pacemaker to the heart.

Pacemakers deliver pacing pulses to the heart to cause the stimulated heart chamber to contract when the patient's own intrinsic rhythm fails. To this end, pacemakers include sensing circuits that sense cardiac activity for the detection of intrinsic cardiac events such as intrinsic atrial events (P waves) and intrinsic ventricular events (R waves). By monitoring such P waves and/or R waves, the pacemaker circuits are able to determine the intrinsic rhythm of the heart and provide stimulation pacing pulses that force atrial and/or ventricular depolarization at appropriate times in the cardiac cycle when required to help stabilize the electrical rhythm of the heart.

Pacemakers are described as single-chamber or dual-chamber systems. A single-chamber system stimulates and senses the same chamber of the heart (atrium or ventricle). A dual-chamber system stimulates and/or senses in both chambers of the heart (atrium and ventricle). Dual-chamber systems may typically be programmed to operate in either a dual-chamber mode or a single-chamber mode.

In determining whether all the leads of an implantable cardiac stimulation device are functional, that is, the leads are not shorted or open, such devices may include a lead supervision function block, incorporated into the hardware and/or the software, that determines the resistance between the leads. In the case where a lead is non-functional, the device switches to other leads for sensing and stimulating the heart.

To implement lead supervision function in prior devices, pulse voltage and pulse current are measured substantially simultaneously through a measured data system. The lead impedance is calculated by dividing the measured voltage by the measured current. The division operation is usually done using additional hardware or computer software. Division operations in the software requires significant processing time and power consumption for the pacemaker circuits because it is performed via the pacemaker's microprocessor. In addition, if the division operation is performed using a dedicated digital hardware, it requires a significant number of logic gates (on the order of a few thousand logic gates) which take up significant chip real estate area. The elimination of either software or a dedicated digital hardware implementation of the division operation is desirable.

SUMMARY OF THE INVENTION

The present invention provides a circuit that monitors impedance of an electrode configuration including first and second electrodes in electrical contact with a heart. The circuit is within an implantable cardiac stimulation device which applies stimulation pulses having a current and a voltage magnitude across the electrode configuration.

In accordance with one aspect of the invention, the circuit that monitors impedance of the electrode configuration includes a current sensing circuit that provides a first analog signal representing the magnitude of the current of a stimulation pulse applied to the electrode configuration, a voltage sensing circuit that provides a second analog signal representing the magnitude of the voltage of the stimulation pulse applied to the electrode configuration, and an impedance determining circuit having an analog input coupled to one of the current sensing circuit and the voltage sensing circuit for receiving one of the first and second signals, an analog reference input coupled to the other one of the current sensing circuit and the voltage sensing circuit for receiving the other one of the first and second signals, and a digital output for providing a digital signal proportional to the ratio of the first and second signals.

In accordance with another aspect of the invention, the impedance determining circuit is an analog to digital (A/D) converter. The analog input of the A/D converter is coupled to the current sensing circuit to receive the first signal. The analog reference input of the A/D converter is coupled to the voltage sensing circuit to receive the second signal.

In accordance with another aspect of the invention, the circuit further includes an inverter that generates the reciprocal of the digital output of the analog to digital converter.

In accordance with another aspect of the invention, the current sensing circuit and the voltage sensing circuit include an amplifier.

In accordance with another aspect of the invention, in an implantable cardiac stimulation device, a method of monitoring impedance of an electrode configuration of an implantable cardiac stimulation device, the electrode configuration including first and second electrodes in electrical contact with a heart, the method includes the steps of applying a stimulation pulse to the electrode configuration, the stimulation pulse having a current and voltage magnitude, generating a first analog signal representing the current magnitude of the stimulation pulse applied to the electrode configuration, providing a second analog signal representing the voltage magnitude of the stimulation pulse applied to the electrode configuration, and deriving directly from the first and second analog signals a digital output signal having a value proportional to the ratio of the first analog signal and the second analog signal.

In accordance with a further embodiment of the present invention, the first analog signal may represent the voltage magnitude and the second analog signal may represent the current magnitude applied to the electrode.

In accordance with another aspect of the invention, the deriving step of the method includes applying the first and second analog signals to an analog to digital converter. The deriving step further includes coupling an analog input of the analog to digital converter to receive the first signal, coupling an analog reference input of the analog to digital converter to receive the second signal, and generating the reciprocal of the digital output of the analog to digital converter.

In accordance with another aspect of the invention, the method includes the further step of amplifying the first analog signal prior to the deriving step.

In accordance with another aspect of the invention, the method includes the further step of amplifying the second analog signal prior to the deriving step.

BRIEF DESCRIPTION OF THE DRAWINGS

Further features and advantages of the present invention may be more readily understood by reference to the following description taken in conjunction with the accompanying drawings, in which.

DESCRIPTION OF THE PREFERRED EMBODIMENTS

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
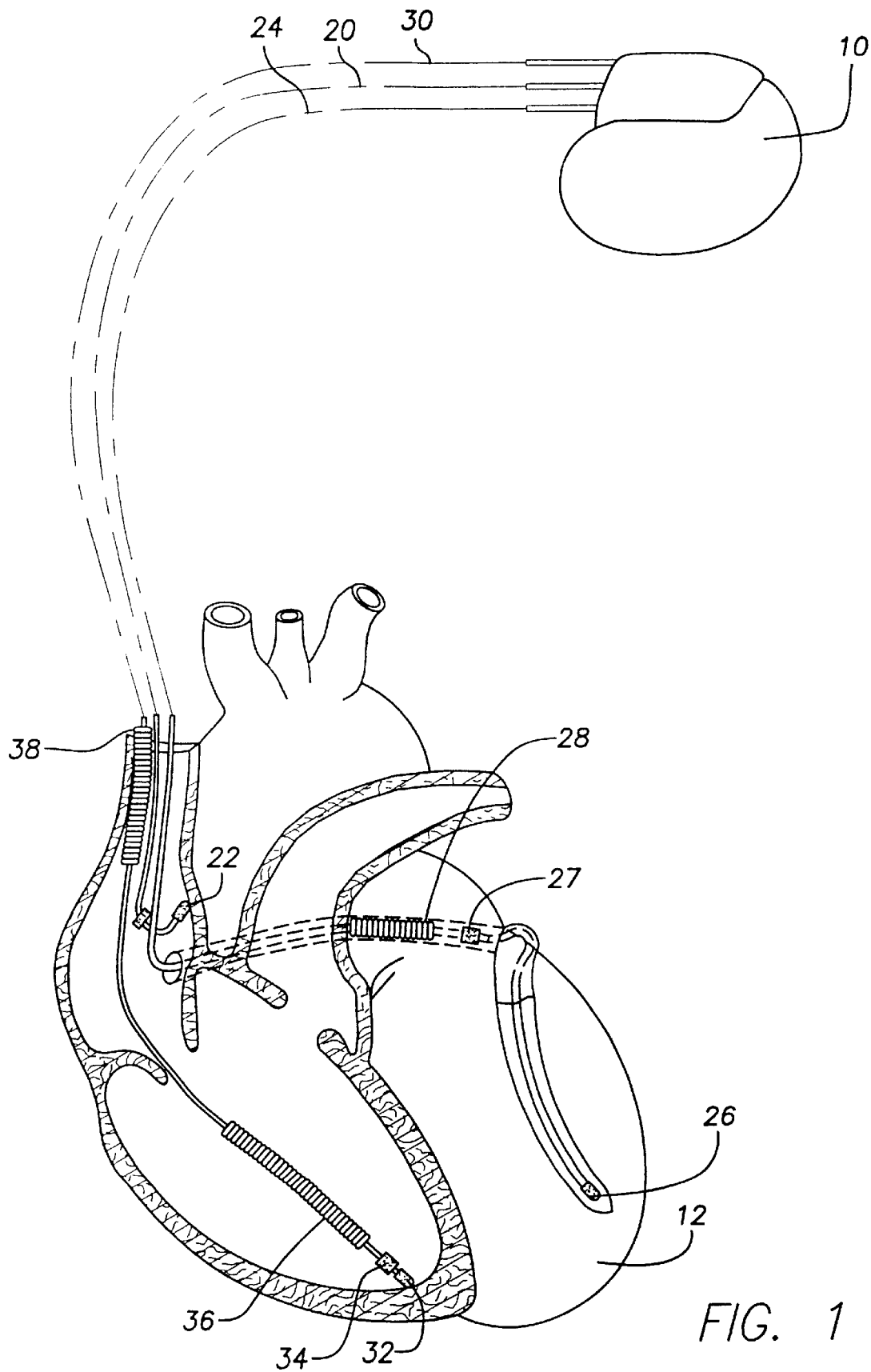
FIG. 1 is a simplified diagram illustrating an implantable stimulation device embodying the present invention in electrical communication with one or more leads implanted into a patient's heart for delivering single-chamber or multi-chamber stimulation and/or shock therapy.

As shown in FIG. 1, there is a stimulation device 10 in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left chamber pacing therapy, the stimulation device 10 is coupled to a "coronary sinus" lead 24 designed for placement in the "coronary sinus region" via the coronary sinus ostium for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the heart.

Figure 2:
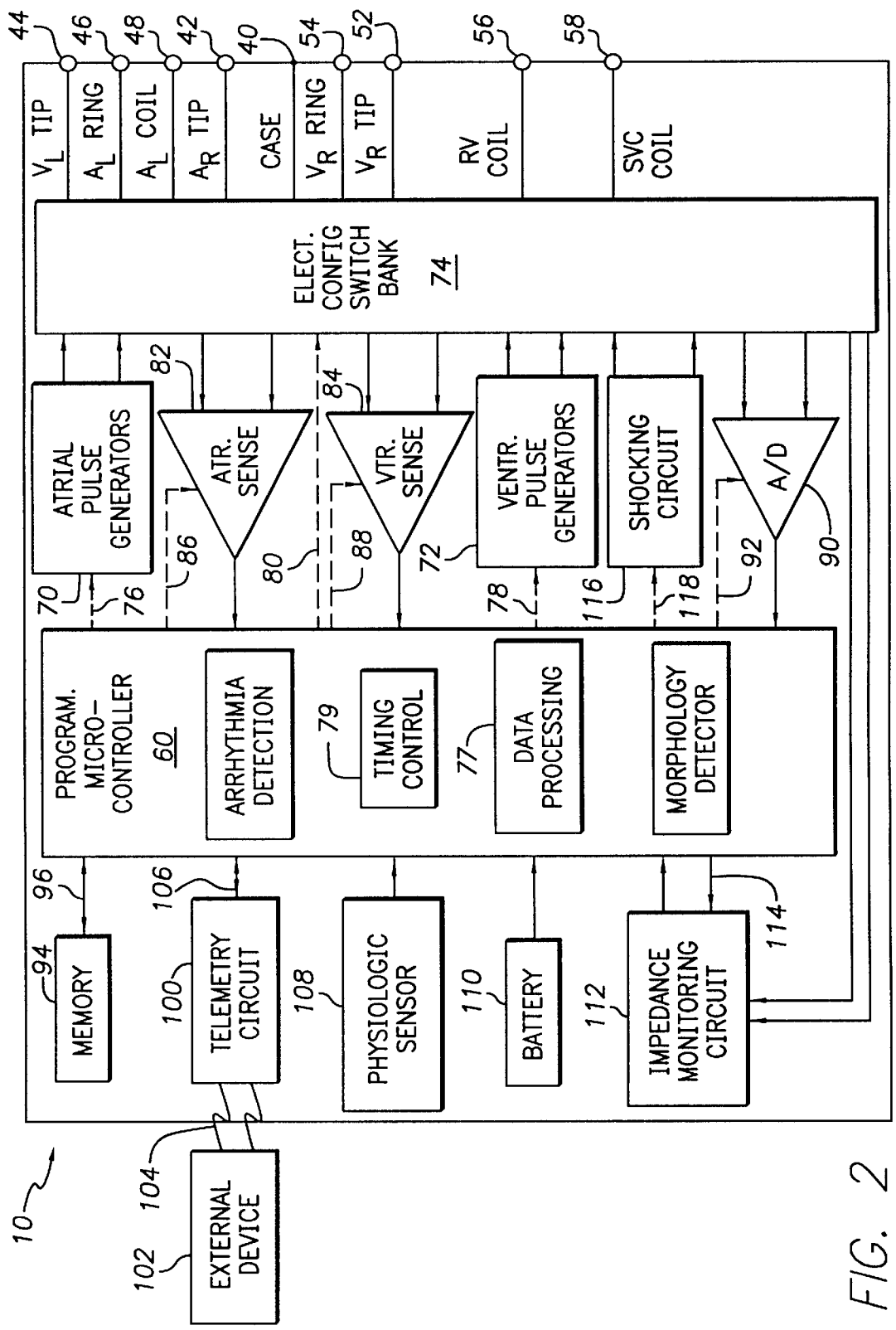
FIG. 2 is a functional block diagram of a multi-chamber implantable stimulation device embodying the present invention illustrating the basic elements of a stimulation device which can provide cardioversion, defibrillation and pacing stimulation in one or more chambers of the heart.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular ring electrode 26, the left atrial tip electrode 27, and the left atrial coil electrode 28, respectively.

To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and may further include RAM and/or ROM memory, logic and timing circuitry, state machine circuitry, and I/O circuitry. Typically, the microcontroller 60 includes the ability to process and/or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A—A) interval, or ventricular interconduction (V—V) interval, etc.) as well as to keep track of the timing of refractory periods, blanking intervals, noise detection windows, evoked response windows, alert intervals, marker channel timing, etc., which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the configuration of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing configuration" of the cardiac signal by selectively closing the appropriate switches, as is also known in the art. In this way, the clinician may program the sensing configuration independent of the stimulation configuration.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode configuration, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104.

In the preferred embodiment, the stimulation device 10 further includes a physiologic sensor 108, commonly referred to as a "rate-responsive" sensor because it is typically used to adjust pacing stimulation rate according to the activity of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V—V interval, etc.) at which the atrial and ventricular pulse generators, 70 and 72, generate stimulation pulses.

The stimulation device additionally includes a battery 110 which provides operating power to all of the circuits shown in FIG. 2. For the stimulation device 10, which employs shocking therapy, the battery 110 must be capable of operating at low current drains for long periods of time, and then be capable of providing high-current pulses (for capacitor charging) when the patient requires a shock pulse. The battery 110 must also have a predictable discharge characteristic so that elective replacement interval can be detected. Accordingly, the device 10 preferably employs lithium/silver vanadium oxide batteries for defibrillation and lithium iodine batteries for pacing as are known in the art.

In the case where the stimulation device 10 is intended to include cardioversion/defibrillation functionality, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 Joules), moderate (0.5–10 Joules), or high energy (11 to 40 Joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 Joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

As further shown in FIG. 2, the device 10 is shown as having an impedance monitoring circuit 112 which is enabled by the microcontroller 60 via a control signal 114. The known uses for an impedance monitoring circuit 112 include, but are not limited to, lead impedance surveillance during the acute and chronic phases for proper lead positioning or dislodgment; detecting in-operable electrodes and automatically switching to an operable pair if dislodgment occurs; measuring respiration or minute ventilation; measuring thoracic impedance for determining shock thresholds; measuring stroke volume; and detecting the opening of heart valves. The impedance monitoring circuit 112 is advantageously coupled to the switch 74 so that the impedance of any desired electrode configuration may be monitored. For example, but not limited to these examples, impedance monitoring can occur between the right ventricular tip electrode 52 and the case 40, or impedance monitoring can occur between the right ventricular tip electrode 52 and the right ventricular coil electrode 56. The digital output of the impedance monitoring circuit 112 is sent to the data processing circuit 77 of the microcontroller 60. If impedance measurements for an electrode configuration are outside a preset acceptable range of values, the data processing circuit 77 signals the electrode configuration switch 74 to change to another electrode configuration when possible because dislodgment of or damage to an electrode may exist. The data processing circuit 77 may also cause the telemetry circuit 100 to signal an alarm to notify the patient or the patient's physician that a problem with lead integrity has been detected.

Figure 3:
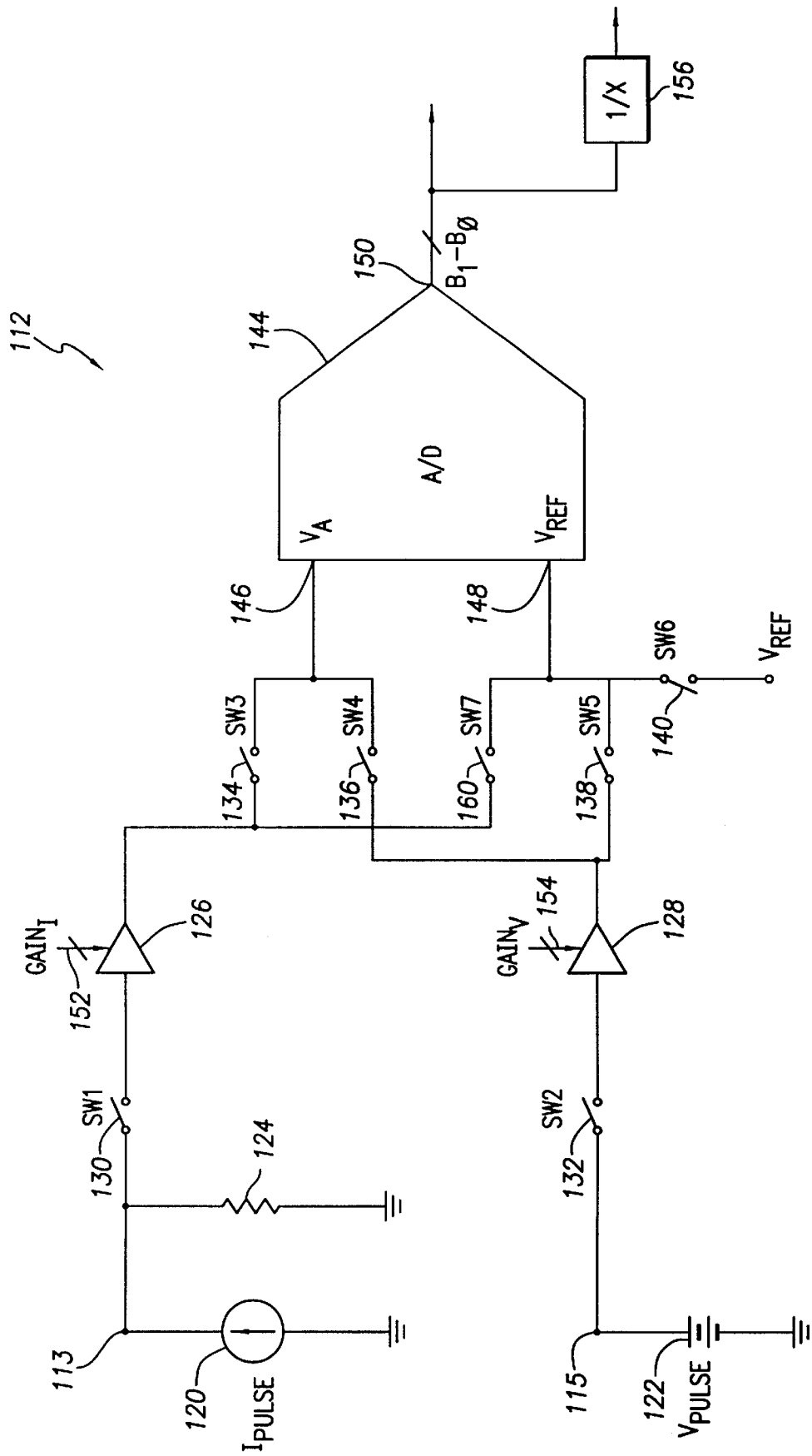
FIG. 3 is a schematic circuit diagram of an impedance monitoring circuit embodying the present invention and which may be used in the device of FIGS. 1 and 2.

An impedance monitoring circuit 112 embodying the present invention is shown in FIG. 3 in greater detail. The circuit 112 has input terminals 113 and 115 for connection by the switch 74 to the electrode configuration of the device 10 to be tested. Illustrated in FIG. 3 is a current source 120 representing the current signal ($I_{pulse}$) of an applied stimulation pulse and a voltage source 122 representing the voltage signal ($V_{pulse}$) of the applied stimulation pulse.

The impedance monitoring circuit 112 includes a resistor 124 ($R_{prox}$), a pair of amplifiers 126 and 128 ($I_{Amp}$ and $V_{Amp}$), switches 130, 132, 134, 136, 138, and 140 (SW1, SW2, SW3, SW4, SW5, and SW6 respectively), a dc voltage reference terminal 142 ($V_{REF}$) and an analog-to-digital (A/D) converter 144. The A/D converter has an analog current input 146 ($V_A$), an analog reference voltage input 148 ($V_{REF}$) and a digital output 150 providing output bits b7–b0. The resistor 124 is coupled between the input terminal 113 and common potential and is set at a known value of, for example, between 5 and 10 ohms.

The purpose of the amplifiers is to sample-and-hold, to ac condition (amplify or attenuate), and to dc condition the signals before they are fed into the A/D converter in a manner known in the art. Also in a known manner, the gain of current amplifier 126 ($Gain_I$) and the gain of voltage amplifier 128 ($Gain_V$) may be selected by software at inputs 152 and 154 in the microprocessor according to programmed values. As a result, amplifier 126 provides a first signal representing the magnitude of the current of a stimulation pulse and amplifier 128 provides a second signal representing the magnitude of the voltage of the stimulation pulse. The A/D converter 144 inputs the conditioned analog first and second signals. As is known in the art, the value of the digital output bits of an A/D converter is proportional to the ratio of analog input signal at input 146 to the input dc voltage reference at input 148. This is utilized to advantage in accordance with this embodiment. As will be seen hereinafter, with switches 130, 132, 134 and 138 closed and switches 136 and 140 open, the output of the A/D converter 144 is a digitized representation of the ratio of the $I_{pulse}$ signal to the $V_{pulse}$ signal.

In accordance with this embodiment of the present invention, when the impedance of an electrode configuration is to be measured, the microprocessor 60, over control line 114, closes switches 130 (SW1), 132 (SW2), 134 (SW3), and 138 (SW5) and opens switches 136 (SW4) and 140 (SW6). Reference may be made to Table 1 for the switch conditions.

When the stimulation pulse is delivered, a first analog input signal is generated by amplifier 126 and is conveyed to input 146 of the analog to digital converter 144. The first analog signal thus produced has a magnitude representing the magnitude of the current of the stimulation pulse.

A second analog signal is simultaneously produced by the amplifier 128. The second analog signal represents the voltage of the stimulation pulse and is applied to the voltage reference input 148 of the analog to digital converter.

The digital output of the A/D converter 144 is proportional to the inverse of the lead impedance or admittance of the electrode configuration because the digital output of the A/D converter 144 provides a digital signal proportional to the ratio of the first analog signal at input 146 from the current sensing circuit to the second analog signal at input 148 from the voltage sensing circuit. In accordance with an alternate embodiment, the reciprocal of the digital output of the A/D converter 144 may be generated by an inverter 156 (1/x) to obtain an output directly proportional to the lead impedance across the electrode configuration.

The digital output signal from the A/D converter 144 is sent to the data processing circuit 77 within the microprocessor. The data processing circuit 77 compares the digital output signal to an expected normal range. If lead impedance values are outside the normal range, the data processing circuit may signal the electronic configuration switch 74 to change to another electrode configuration.

In accordance with this embodiment of the present invention, separate measurements of $I_{pulse}/V_{REF}$ and $V_{pulse}/V_{REF}$ are not necessary. Lead impedance is a digital value from the A/D converter measured as the inverse of the ratio of the $I_{pulse}/V_{pulse}$ analog signal. The digital output bits represent lead impedance according to the equation:

$$(I_{pulse} \times R_{prox}/V_{pulse}) \times (Gain_I/Gain_V) = (R_{prox}/R_{lead}) \times (Gain_I/Gain_V).$$

The values for $R_{prox}$, $Gain_I$, and $Gain_V$ are known values set by hardware and/or software. The value for $R_{lead}$ is the impedance of the stimulation lead, wherein $R_{lead} = V_{pulse}/I_{pulse}$.

As will be appreciated by those skilled in the art, the first and second analog signals applied to the A/D converter may be reversed to provide a digital output from the A/D converter that is directly proportional to the lead impedance (V/I). This, however, is not the preferred mode since the A/D converter would not function properly if the voltage applied to the $V_{REF}$ input 148 is zero. This could be the case if applied current is coupled to input 148 when the lead is open circuited. Thus, it is advisable to connect the signal representing the voltage amplitude to input 148. As a further advantage, this voltage is known by the microprocessor to assist in qualifying the correctness of the result. However, for purposes of completeness, Table 1 also includes the switch conditions when the inputs to the A/D converter are set to provide an output directly proportional to lead impedance (V/I).

The stimulation voltage across an electrode configuration may also be measured by the circuit 112. Here, the microprocessor 60, over control line 114, closes switches 132 (SW2), 136 (SW4), and 140 (SW6) and opens switches 130 (SW1), 134 (SW3) and 138 (SW5). Reference may be made to Table 1 for the switch conditions.

When the stimulation pulse is delivered, a first analog input signal is generated by amplifier 128 and is conveyed to input 146 of the analog to digital converter 144. The first analog signal thus produced has a magnitude representing the magnitude of the voltage of the stimulation pulse.

A second analog signal is produced at the dc voltage reference terminal 142. The second analog signal represents the reference voltage and is applied to the voltage reference input 148 of the analog to digital converter.

The digital output of the A/D converter 144 is proportional to the pulse voltage of the electrode configuration because the digital output of the A/D converter 144 provides a digital signal proportional to the ratio of the first analog signal at input 146 from the voltage sensing circuit to the second analog signal at input 148 from the voltage reference circuit.

The digital output signal from the A/D converter 144 is sent to the data processing circuit 77 within the microprocessor. The data processing circuit 77 compares the digital output signal to an expected normal range. If pulse voltage values are outside the normal range, the data processing circuit may signal the electronic configuration switch 74 to change the electrode configuration.

The digital output bits represent pulse voltage ($V_{pulse}$) according to the equation:

$$(V_{pulse}/V_{REF}) \times Gain_V.$$

The stimulation current of an electrode configuration may also be measured by the circuit 112. Here, the microprocessor 60, over control line 114, closes switches 130 (SW1), 134 (SW3), and 140 (SW6) and opens switches 132 (SW2), 136 (SW4) and 138 (SW5). Reference may be made to Table 1 for the switch conditions.

When the stimulation pulse is delivered, a first analog input signal is generated by amplifier 126 and is conveyed to input 146 of the analog to digital converter 144. The first analog signal thus produced has a magnitude representing the magnitude of the current of the stimulation pulse.

A second analog signal is produced at the dc voltage reference terminal 142. The second analog signal represents the reference voltage and is applied to the voltage reference input 148 of the analog to digital converter.

The digital output of the A/D converter 144 is proportional to the pulse current of the electrode configuration because the digital output of the A/D converter 144 provides a digital signal proportional to the ratio of the first analog signal at input 146 from the current sensing circuit to the second analog signal at input 148 from the voltage reference circuit.

The digital output signal from the A/D converter 144 is sent to the data processing circuit 77 within the microprocessor. The data processing circuit 77 compares the digital output signal to an expected normal range. If pulse current values are outside the normal range, the data processing circuit may signal the electronic configuration switch 74 to change the electrode configuration.

The digital output bits represent pulse current (Ipulse) according to the equation:

$$(I_{pulse}/V_{REF}) \times R_{prox} \times Gain_V.$$

TABLE 1

Circuit Switch Configuration

|  | SW1 | SW2 | SW3 | SW4 | SW5 | SW6 | SW7 |
|---|---|---|---|---|---|---|---|
| During $V_{pulse}$ measurement | Open | Closed | Open | Closed | Open | Closed | Open |
| During $I_{pulse}$ measurement | Closed | Open | Closed | Open | Open | Closed | Open |
| During lead impedance measurement | | | | | | | |
| I/V | Closed | Closed | Closed | Open | Closed | Open | Open |
| V/I | Closed | Closed | Open | Closed | Open | Open | Closed |

While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

What is claimed is:

1. In an implantable cardiac stimulation device which applies stimulation pulses having a current and a voltage magnitude across an electrode configuration including first and second electrodes in electrical contact with a heart, circuitry that monitors impedance of the electrode configuration comprising:

a current sensing circuit that provides a first analog signal representing the magnitude of the current of a stimulation pulse applied to the electrode configuration;

a voltage sensing circuit that provides a second analog signal representing the magnitude of the voltage of the stimulation pulse applied to the electrode configuration; and an impedance determining circuit having an analog input coupled to one of the current sensing circuit or the voltage sensing circuit for receiving one of the first or second signals, an analog reference input coupled to the other one of the current sensing circuit or the voltage sensing circuit for receiving the other one of the first or second signals, and a digital output for providing a digital signal proportional to the ratio of the first and second signals.

2. The circuitry of claim 1, wherein the impedance determining circuit is an analog to digital converter.

3. The circuitry of claim 2, wherein the analog input is coupled to the current sensing circuit to receive the first signal, the analog reference input is coupled to the voltage sensing circuit to receive the second signal, and the circuitry further includes an inverter that generates the reciprocal of digital output of the analog to digital converter.

4. The circuitry of claim 1, wherein the current sensing circuit comprises an amplifier.

5. The circuitry of claim 1, wherein the voltage sensing circuit comprises an amplifier.

6. In an implantable cardiac stimulation device which applies stimulation pulses having a current and a voltage magnitude across an electrode configuration including first and second electrodes in electrical contact with a heart, impedance monitoring means for monitoring impedance of the electrode configuration comprising:

current sensing means for providing a first analog signal representing the magnitude of the current of a stimulation pulse applied to the electrode configuration;

voltage sensing means for providing a second analog signal representing the magnitude of the voltage of the stimulation pulse applied to the electrode configuration; and impedance determining means having analog input means coupled to one of the current sensing means or the voltage sensing means for receiving one of the first or second signals, analog reference input means coupled to the other one of the current sensing means or the voltage sensing means for receiving the other one of the first or second signals, and digital output means for providing a digital signal proportional to the ratio of the first and second signals.

7. The impedance monitoring means of claim 6, wherein the impedance determining means is an analog to digital converter.

8. The impedance monitoring means of claim 6, wherein the analog input means is coupled to the current sensing means to receive the first signal, the analog reference input means is coupled to the voltage sensing means to receive the second signal, and the impedance monitoring means further includes an inverter means for providing the reciprocal of the digital output of the analog to digital converter.

9. The impedance monitoring means of claim 6, wherein the current sensing means comprises an amplifier.

10. The impedance monitoring means of claim 6, wherein the voltage sensing means comprises an amplifier.

* * * * *